United States Patent [19]

Galliani et al.

[11] Patent Number: 5,219,873
[45] Date of Patent: Jun. 15, 1993

[54] COMPOUNDS OF 1,2,5,6-TETRAHYDROPYRIDINE WHICH ARE USEFUL AS CHOLINERGIC AGENTS

[75] Inventors: Giulio Galliani; Fernando Barzaghi, both of Monza; Carla Bonetti, Fontanella; Emilio Toja, Milano, all of Italy

[73] Assignee: Roussel UCLAF, Paris, France

[21] Appl. No.: 408,441

[22] Filed: Sep. 15, 1989

Related U.S. Application Data

[63] Continuation of Ser. No. 184,139, Apr. 21, 1988, abandoned.

Foreign Application Priority Data

Apr. 24, 1987 [IT] Italy .................. 20260 A87

[51] Int. Cl.$^5$ .................. A61K 31/44; C07D 211/70
[52] U.S. Cl. .................. 514/357; 546/335; 546/338
[58] Field of Search .......... 546/338, 335; 514/357

[56] References Cited

U.S. PATENT DOCUMENTS

| | | | |
|---|---|---|---|
| 3,004,979 | 10/1961 | Druey et al. | 546/338 |
| 4,710,508 | 12/1987 | Bergmeir | 514/357 |
| 4,786,648 | 11/1988 | Bergmeier et al. | 514/357 |

*Primary Examiner*—C. Warren Ivy
*Assistant Examiner*—Zinna Northington-Davis
*Attorney, Agent, or Firm*—Stevens, Davis, Miller & Mosher

[57] ABSTRACT

Compounds useful in the treatment of Alzheimer's disease, senile dimentia and memory disorders of the formula

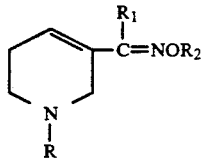

in which R represents hydrogen, hydroxyl, a linear, branched or cyclic, saturated or unsaturated, alkyl, containing up to 8 carbon atoms, possibly substituted by free or esterified carboxy or R represents aralkyl containing up to 10 carbon atoms or —COOZ in which Z represents a linear, branched or cyclic saturated or unsaturated, alkyl containing up to 8 carbon atoms and $R_2$ represents hydrogen or a linear or branched, saturated or unsaturated alkyl containing up to 8 carbon atoms, $COalk_1$ radical or $(CH_2)_2N(alk_2)_2$, $alk_1$ and $alk_2$ representing an alkyl containing up to 8 carbon atoms, as well as their addition salts with acids provided that if R represents an alkyl $R_2$ does not represent hydrogen; also therapeutic compositions containing at least one said compound and method of treating patients with said compounds.

7 Claims, No Drawings

COMPOUNDS OF 1,2,5,6-TETRAHYDROPYRIDINE WHICH ARE USEFUL AS CHOLINERGIC AGENTS

This application is a continuation of application Ser. No. 07/184,139, filed Apr. 21, 1988, now abandoned.

The present invention relates to new derivatives of 1,2,5,6-tetrahydropyridine and their salts, the process for preparing them, their use as medicaments and compositions containing them.

More particularly, the invention relates to compounds of the formula (I):

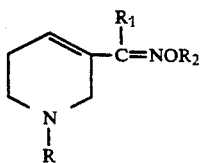

in which R represents hydrogen, hydroxyl, a linear, branched or cyclic, saturated or unsaturated, alkyl, containing up to 8 carbon atoms, possibly substituted by a free or esterified carboxy, or R represents aralkyl containing up to 10 carbon atoms or —COOZ in which Z represents a linear, branched or cyclic, saturated or unsaturated, alkyl, containing up to 8 carbon atoms or aralkyl containing from 7 to 10 carbon atoms, $R_1$ represents a linear, branched or cyclic, saturated or unsaturated, alkyl containing up to 8 carbon atoms and $R_2$ represents hydrogen or a linear or branched, saturated or unsaturated alkyl containing up to 8 carbon atoms, $COalk_1$ or $(CH_2)_2N(alk_2)_2$, $alk_1$ and $alk_2$ representing an alkyl containing up to 8 carbon atoms, as well as their addition salts with acids, provided that if R represents alkyl, $R_2$ does not represent hydrogen.

Among the addition salts with acids, there can be cited those formed with mineral acids, such as hydrochloric, hydrobromic, sulphuric or phosphoric acids, or with organic acids, such as formic, acetic, propionic, benzoic, maleic, fumaric, succinic, tartaric, citric, oxalic, glyoxylic, aspartic, alkanesulphonic, such as methane- or ethanesulphonic, arylsulphonic, such as benzene- or paratoluene-sulphonic acids.

When R, $R_1$, $R_2$ or Z represents a saturated, linear or branched alkyl, it is preferred that it be methyl, ethyl, n-propyl, isopropyl, n-butyl, sec-butyl, isobutyl, n-pentyl or n-hexyl.

When R, $R_1$, $R_2$ or Z represents an unsaturated alkyl radical, it is preferred that it be ethylenic radical such, for example, an allyl or 1,1-dimethylallyl radical, or an acetylene radical such, for example, as an ethynyl or propynyl radical.

When R, $R_1$ or Z represents a cyclic alkyl radical, it is preferred that it be cyclopropyl, cyclobutyl, cyclopentyl or cyclohexyl.

When R or Z represents aralkyl, it is preferred that it be benzyl.

$alk_1$ and $alk_2$ preferably represent methyl, ethyl, n-propyl, isopropyl, n-butyl, sec-butyl or isobutyl.

The compounds of the formula (I) in which R represents alkyl and $R_2$ hydrogen, notably 1-methyl-4-acetyl-1,2,5,6-tetrahydropyridin-oxime, are known for their parasympathomimetic properties (see U.S. Pat. No. 3,004,979).

The compounds of the invention present quite unexpected pharmacological properties in view of said patent, which are very interesting as are shown by the results of biological tests summarized below.

The invention has particularly as its object the compounds with the formula (I) in which $R_1$ represents linear alkyl containing from 1–4 carbon atoms, for example, methyl.

Among the preferred compounds of the invention, there can be cited the compounds with the formula (I) in which R represents hydrogen, as well as those in which R represents hydroxyl and those in which R represents linear or branched, saturated or unsaturated alkyl, containing from 1 to 4 carbon atoms, such, for example, methyl, ethyl, propyl or allyl, as well as their addition salts with acids.

There can also be cited the compounds with the formula (I) in which $R_2$ represents hydrogen, those in which $R_2$ represents alkyl containing from 1 to 4 carbon atoms and notably methyl.

The invention has more particularly as its object the compounds of which the preparation is given below, and quite especially the products of examples 2, 3 and 12.

The compounds of the invention notably display an important cholinomimetic activity of long duration, by oral route.

The products further display a strong dissociation between the central activity and the peripheral activity, as is shown by the results of the tests set out below.

Therefore, an object of the invention is the claimed compounds as medicaments, useful in particular in the treatment of Alzheimer's disease or of senile dementia and equally in the treatment of memory disorders.

It is well known that disorders of learning and of memory in aged persons are connected above all with a deficiency in the central cholinergic system, particularly in senile dementia and Alzheimer's disease.

It is therefore evident that products having a central cholinergic action could be employed in the therapeutic treatment of these diseases (Bartus, R. I., Science 217, 408, 1982).

It has been demonstrated that arecoline injected by intravenous route has a positive effect on patients having a memory defect (Sitaram N. et al., Science 201, 274, 1978), (Christie J. E. et al. Brit. J. Psychiatry, 138, 46, 1981).

A limitation to the therapeutic use of arecoline is the fact that this product has a very weak activity by oral route and a short duration of action.

The products which are the subject of the invention, after administration by oral route, have shown a central cholinomimetic activity much superior to that of arecoline and with a longer duration of action.

The usual posology is variable according to the affection concerned, the subject treated and the administration route; it can be between 50 mg and 300 mg per day, for example, between 15 and 150 mg per day in one or more doses for the product of example 3, administered by oral route.

The present invention also has as its subject pharmaceutical compositions containing as the active principle at least one compound of the formula (I). The pharmaceutical compositions of the invention can be solid or liquid and can be presented in the pharmaceutical forms currently used in human medicine, such, for example, as plain or sugar-coated tablets, capsules, granules, suppositories, and injectable preparations. They are prepared according to the usual methods. The active principle or principles can be incorporated in them with the excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, the various wetting, dispersing or emulsifying agents, and preservatives.

The invention also has as its subject a process for the preparation of the compound of the formula (I) in which $R_1$ and $R_2$ have the significance previously indicated and R has the significance previously indicated with the exception of the hydroxyl value, characterized in that a compound with the formula (II):

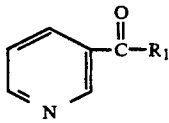
(II)

in which $R_1$ retains the same significance as previously indicated, is submitted to the action of a compound with the formula (III):

(III)

NH$_2$OR'$_2$ or one of its salts, in which R'$_2$ represents hydrogen or a linear or branched, saturated or unsaturated, alkyl containing up to 8 carbon atoms, in order to obtain in the compound with the formula (IV):

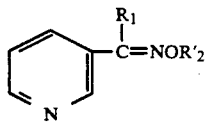
(IV)

which is submitted to the action of an alkyl halide with the formula (V):

R'—Hal  (V)

in which Hal represents halogen and R' represents a linear, branched or cyclic alkyl, saturated or unsaturated, containing up to 8 carbon atoms, possibly substituted by a free or esterified carboxy or R' represents an aralkyl containing up to 10 carbon atoms, in order to obtain the compound with the formula (VI):

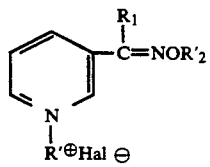
(VI)

which is submitted to the action of a hydrogenation agent, in order to obtain the compound with the formula (I$_A$):

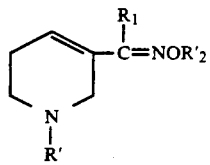
(I$_A$)

in which R', $R_1$ and R'$_2$ are defined as previously which, if required, is either salified, or, if R'$_2$ represents a hydrogen atom, is submitted to the action of a compound with the formula:

R''$_2$—Hal in which Hal represents halogen and R''$_2$ represents COalk$_1$ or —(CH$_2$)$_2$N(Alk$_2$)$_2$, alk$_1$ and alk$_2$ being defined as previously, in order to obtain the corresponding compound with the formula (I$_B$):

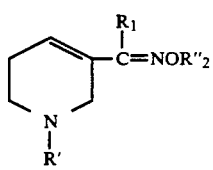
(I$_B$)

in which $R_1$, R' and R''$_2$ are defined as previously which, if required, is salified, or if R' represents an aralkyl radical, compound of formula (I$_A$) or (I$_B$) is submitted to the action of a cleavage agent, in order to obtain the compound with the formula (I$_C$):

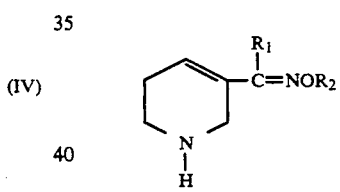
(I$_C$)

in which $R_1$ and $R_2$ are defined as previously, which, if required, is salified, and compounds with the formula (I$_A$) or (I$_B$) in which R' represents aralkyl or (I$_C$) which, if desired, are submitted to the action of an alkyl or aralkyl halogenoformate in order to obtain a compound with the formula (I$_D$):

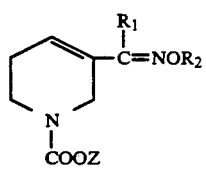
(I$_D$)

in which $R_1$, $R_2$, and Z are defined as previously, which, if required, is salified.

In a preferred mode of conducting the process of the invention:
   the compound with the formula (III) is used in the form of the hydrochloride,
   Hal (in the compound with the formulae R'-Hal or R''$_2$-Hal) represents bromine or iodine,
   the hydrogenation agent is sodium borohydride,
   the cleavage agent is alpha-chloroethoxycarbonyl chloride, the halogenoformate which is used is a chloroformate, for example, of ethyl or of benzyl.

The invention also has as its subject a variant of the preceding process characterized in that a compound with the formula (I'$_A$):

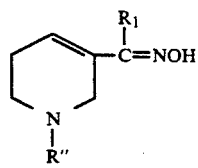

in which R" represents aralkyl containing up to 10 carbon atoms and R$_1$ retains its previous significance is submitted to the action of a silylation agent, in order to obtain the compound with the formula (VII):

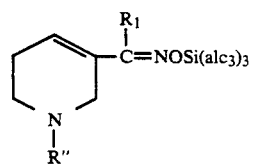

in which alk$_3$ represents alkyl containing from 1 to 8 carbon atoms, which is submitted to the action of a cleavage agent, in order to obtain the compound with the formula (I$_E$):

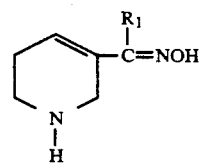

in which R$_1$ is defined as previously, which, if required, is salified.

In a preferred way of realizing this process:
R" represents benzyl,
the silylation agent is trimethylsilyl chloride,
the cleavage agent is alpha-chloroethoxycarbonyl chloride.

The invention also has as its object a process for preparing the compounds with the formula (I) in which R$_1$ and R$_2$ have the previously indicated significance and R represents a hydroxyl radical, characterized in that a compound of the formula (VIII):

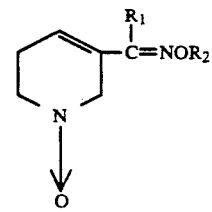

is submitted to the action of a reducing agent in order to obtain a compound with the formula (I$_F$):

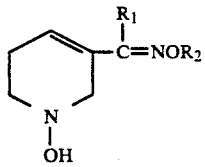

in which R$_1$ and R$_2$ are defined as previously, which, if required, is salified.

In a preferred way of realizing the invention process: the reducing agent is sodium borohydride.

The eventual salification of the products with the formula (I) is carried out according to the usual methods, by making a mineral or organic acid react in sensibly stoechiometric proportions on the said products with the formula (I).

The compounds with the formula (II) are products known in a general way, which can be prepared according to the process described in said U.S. Pat. No. 3,004,979.

The compounds with the formula (VIII) are products described or obtained according to the process described in J. Het. Chem., 16, 1459, 1979.

The following examples illustrate the invention without, however, limiting it.

EXAMPLE 1

3-acetyl-1,2,5,6,-tetrahydropyridine-oxime and its hydrochloride

Stage A: 1-benzyl-3-acetyl-pyridine-oxime bromide.

7.4 g of 3-acetylpyridine oxime is dissolved in 80 cm$^3$ of ethanol, 8 cm$^3$ of benzyl bromide is added to it, with heating at reflux for 6 hours. The solvent is eliminated followed by crystallization from an ether/methanol mixture. 14.21 g of the expected product is obtained. m.p.=200°-201° C.

| Analysis: | | | |
|---|---|---|---|
| Calculated: | C% 54.74 | H% 4.92 | N% 9.19 |
| Found: | 54.56 | 4.98 | 9.07 |

Stage B: 1-benzyl-3-acetyl-1,2,5,6-tetrahydropyridine-oxime.

13.76 g of the product obtained at stage A in solution in 100 cm$^3$ of methanol is cooled to 0° C., 2.54 g of sodium hydroboride is added, the whole is allowed to return to ambient temperature and agitated for 45 minutes. After concentrating under reduced pressure, water is added and extraction is done with chloroform. The organic phase is dried, the solvent is eliminated, and the residue is chromatographed on silica (eluent: ethyl acetate-toluene 8-2). After crystallization of the residue from ethyl acetate, 7.8 g of the expected product is obtained. m.p. 103°-105° C.

| Analysis: | | | |
|---|---|---|---|
| Calculated: | C% 73.01 | H% 7.88 | N% 12.16 |
| Found: | 72.74 | 7.81 | 12.04 |

Stage C: 1-benzyl-3-acetyl-1,2,5,6-tetrahydropyridine-trimethylsilyl oxime.

3.6 g of the product obtained at stage B is dissolved in 60 cm$^3$ of benzene and 1.86 g of 1,4-diazabicyclo [2.2.2.] octane, and over 5 minutes, under an inert atmosphere, 2.07 cm³ of trimethylchlorosilane is added. The suspension is heated to reflux for 3 hours, then cooled, filtered and concentrated to dryness. The residue is taken up in ethyl ether, filtered, the solvent is eliminated under reduced pressure, and 4.5 g of the expected product is obtained.

(b.p. 150° C., under 0.05 mbar)

| Analysis: | | | |
|---|---|---|---|
| Calculated: | C% 67.50 | H% 8.66 | N% 9.26 |
| Found: | 67.33 | 8.59 | 9.19 |

Stage D: 3-acetyl-1,2,5,6-tetrahydropyridine-oxime and its hydrochloride.

Under an inert atmosphere, 20 g of the product obtained as at stage C in solution in 20 cm³ of methylene chloride is cooled to 0° C., 21.6 g of alpha-chloroethyl chloroformate is added, followed by heating to reflux for two-and-a-half hours. After cooling, filtering and eliminating the solvent, the residue is taken up in ethyl ether, triturated and filtered. The solvent is evaporated off, the residue is taken up in methanol, heated to reflux for 30 minutes, then concentrated to dryness. The residue is taken up in methanol and ethyl ether, filtered, crystallized from ethanol, and 2.1 g of the expected product is collected. m.p. 237° C. (with decomposition).

| Analysis: C₇H₁₂N₂O, HCl | | | |
|---|---|---|---|
| Calculated: | C% 47.59 | H% 7.42 | N% 15.86 |
| Found: | 47.74 | 7.38 | 15.78 |

EXAMPLE 2

1-methyl-3-acetyl-1,2,5,6-tetrahydropyridine-O-methyl-oxime and its hydrochloride.

Stage A: 3-acetyl-pyridine-O-methyl-oxime.

6.85 g of methoxyamine hydrochloride is added to 10 g of 3-acetyl pyridine in 50 cm³ of methanol and the whole is heated to reflux for 3 hours. The solvent is eliminated under reduced pressure, the residue is taken up in water, alkanlized with potassium carbonate and extracted with ethyl acetate. After evaporating, 11 g of the expected product is recovered. (b.p.: 115°-118° C. under 18 mm Hg).

Stage B: 1-methyl 3-acetyl-pyridine-O-methyl oxime chloride.

20.5 g of methyl iodide is added to 11 g of the product obtained at stage A in 110 cm³ of ethyl acetate, and the whole is heated to reflux for 3 hours. After cooling, filtering and crystallizing the product from ethanol, 19.3 g of the expected product is obtained. m.p. 155°-157° C.

Stage C: 1-methyl-3-acetyl-1,2,5,6-tetrahydropyridine-O-methyl-oxime and its hydrochloride.

1.7 g of sodium hydroboride is added to a solution of 10 g of the product obtained at stage B in 100 cm³ of methanol and the whole is cooled to +5°/+10° C. After agitating for 1 hour at ambient temperature, the solvent is eliminated under reduced pressure, and the residue is taken up in water, extracted with ethyl ether, and evaporated to dryness. The residue is taken up with ethyl ether, filtered on activated charcoal and salified with gaseous hydrochloric acid. The salt is recrystallized from a mixture of isopropanol and ethyl ether, and 2.8 g of the expected product is obtained. m.p. 169°-171° C.

| Analysis: C₉H₁₆N₂O, HCl | | | |
|---|---|---|---|
| Calculated: | C% 52.80 | H% 8.37 | N% 13.68 |
| Found: | 53.06 | 8.44 | 13.57 |

EXAMPLE 3

3-acetyl-1,2,5,6-tetrahydropyridine-O-methyl-oxime and its hydrochloride

Stage A: 1-benzyl-3-acetyl-pyridine-O-methyl-oxime bromide.

27.8 cm³ of benzyl bromide is added to 23.4 g of the product prepared at stage A of example 2 in solution in 200 cm³ of ethyl acetate. This is heated to reflux for 8 hours, then cooled and filtered, and the solid obtained is crystallized from ethanol. 46 g of the expected product is obtained. m.p. 191°-192° C.

| Analysis: | | | |
|---|---|---|---|
| Calculated: | C% 56.09 | H% 5.34 | N% 8.72 |
| Found: | 56.24 | 5.37 | 8.67 |

Stage B: 1-benzyl-3-acetyl-1,2,5,6-tetrahydropyridine-O-methyl-oxime.

20 g of the product prepared at stage A in solution in 150 cm³ of methanol is cooled to 0° C. At this temperature 3.6 g of sodium borohydride is added, with agitation for 1 hour at ambient temperature. The methanol is eliminated under reduced pressure, the residue is taken up with water, sodium carbonate is added until saturated, and extraction is done with ethyl ether. The organic phase is dried and the solvent is evaporated. 10.66 g of the expected product is obtained. (b.p. 128°-130° C. under 0.4 mbar).

| Analysis: | | | |
|---|---|---|---|
| Calculated: | C% 73.74 | H% 8.25 | N% 11.47 |
| Found: | 73.56 | 8.21 | 11.52 |

Stage C: 1-alpha-chloroethoxycarbonyl-3-acetyl-1,2,5,6-tetrahydropyridine-O-methyl-oxime.

7.2 g of the product obtained at stage B in solution in 100 cm³ of dilchloroethane is cooled to 0° C. and, over 20 minutes, 6.05 g of alpha-chloroethyl chloroformate is added, dissolved in dichloroethane. After heating to reflux for one-and-a-half hours, cooling and filtering, the solvent is eliminated under reduced pressure. The residue is taken up in ethyl ether and filtered again. The solvent is evaporated off, and 8.44 g of product is obtained which is utilized as it is for the following stage. (b.p. 210° C. under 0.06 mbar).

| Analysis: | | | |
|---|---|---|---|
| Calculated: | C% 50.68 | H% 6.57 | N% 10.75 |
| Found: | 50.86 | 6.46 | 10.59 |

Stage D: 3-acetyl-1,2,5,6-tetrahydropyridine-O-methyl-oxime and its hydrochloride.

The product obtained at stage C in 70 cm³ of methanol is heated to reflux for 2 hours, then cooled, evaporated to dryness, and the residue is crystallized from ethanol. 3.9 g of the expected product is obtained, m.p. 199°-200° C. Using the process of example 2 the expected hydrochloride is obtained.

| Analysis: | | | |
|---|---|---|---|
| Calculated: | C% 50.39 | H% 7.93 | N% 14.69 |
| Found: | 50.31 | 7.84 | 14.55 |

EXAMPLE 4

1-methyl-3-acetyl-1,2,5,6-tetrahydropyridine-O-ethyl-oxime and its hydrochloride.

Stage A: 3-acetyl-pyridine-O-ethyl-oxime.

4.8 cm$^3$ of 3-acetyl pyridine is dissolved in 50 cm$^3$ of methanol, to this 4.27 g of orthoethyl hydroxylamilne hydrochloride is added and the whole is taken to reflux for 3 hours, then cooled and evaporated to dryness under reduced pressure. The residue is taken up with water, neutralized with sodium bicarbonate and extracted with ethyl acetate. The extracts are dried and concentrated to dryness under reduced pressure. 6.9 g of the expected product is obtained, utilisable for the following stage. m.p. 160°-162° C., crystallized from an etherisopropanol mixture in the form of the hydrochloride.

Stage B: 1-methyl-3-acetyl-pyridine-O-ethyl-oxime iodide.

A mixture of 5.3 g of the product obtained at stage A and 4.1 cm$^3$ of methyl iodide is agitated for 8 hours at reflux in 80 cm$^3$ of ethanol, then distilled to dryness. 9.3 g of the expected product is obtained. m.p. 95° C., crystallized from an ether-isopropanol mixture.

Stage C: 1-methyl-3-acetyl-1,2,5,6-tetrahydropyridine-O-ethyl-oxime and its hydrochloride.

1.7 g of boron and sodium hydride is added to a solution of 9.1 g of the product obtained at stage B in 90 cm$^3$ of methanol, maintained at 5° C. After 4 hours at ambient temperature, this is evaporated to dryness under reduced pressure. The residue is taken up with water, extracted with ethyl acetate, and concentrated to dryness under reduced pressure. The residue is taken up with water, extracted with ethyl acetate, and the extracts are concentrated to dryness under reduced pressure. The residue is chromatographed on silica gel (eluent: chloroform-methanol 5-1). The 3.5 g of oil obtained is dissolved in ether and salified with gaseous hydrochloric acid. After evaporating to dryness, 3.7 g of the expected product is obtained. m.p. 186°-188° C., recrystallized from an isopropanol-ether mixture.

| Analysis: | | | |
|---|---|---|---|
| Calculated: | C% 54.91 | H% 8.76 | N% 12.81 |
| Found: | 54.88 | 8.94 | 12.76 |

EXAMPLE 5

3-acetyl-1,2,5,6-tetrahydropyridine-O-ethyl-oxime and its hydrochloride

Stage A: 1-N-benzyl-3-acetyl-pyridine-O-ethyl-oxime bromide.

6.9 g of the product obtained at stage A of example 4 is dissolved in 70 cm$^3$ of ethanol, 6 cm$^3$ of benzyl bromide is added, and the whole is heated to reflux for 6 hours, then cooled, evaporated under reduced pressure, and 13.9 g of the expected product is isolated from the ether.

Stage B: 1-N-benzyl-3-acetyl-1,2,5,6-tetrahydropyridine-O-ethyl oxime.

(a) To a solution of 0.8 g of sodium in 50 cm$^3$ of ethanol, 3.8 g of the product obtained at stage B of example 1 and 1.25 cm$^3$ of bromoethane are added and the whole is taken to reflux for 3 hours, then cooled and concentrated to dryness. 2.84 g of the expected product is obtained, after elution on a column (eluent: ethyl acetate-toluene, 3-2). (b.p. 180°-190° C. under 0.05 mbar).

(b) The product can also be obtained with a yield of 71% by reduction with boron and sodium hydride, operating as at stage B of example 1, starting with the product obtained at stage A of example 5.

Stage C: 3-acetyl-1,2,5,6-tetrahydropyridine-O-ethyl-oxime and its hydrochloride.

2.7 g of the product obtained at stage B is dissolved in 50 cm$^3$ of dichloroethane, then, at 0° C., 1.8 g of alpha-chloroethyl-chloro-formate is added; the whole is taken to reflux for 1 hour 30 minutes, then evaporated to dryness and taken up with ether. The insoluble matter is filtered off and evaporated to dryness under reduced pressure. The residual oil is taken up with 40 cm$^3$ of methanol, taken to reflux for 1 hour 30 minutes, then evaporated to dryness. The residue is taken up with ether, filtered, and 4.2 g of the expected base is isolated and crystallized from an ether-methanol mixture. m.p. 198°-199° C. (decomposition). Using the process of example 2 the expected hydrochloride is obtained.

| Analysis: | | | |
|---|---|---|---|
| Calculated: | C% 52.81 | H% 8.37 | N% 13.69 |
| Found: | 52.59 | 8.25 | 13.48 |

EXAMPLE 6

3-acetyl-1,2,5,6-tetrahydropyridine-O-2-propynyloxime and its hydrochloride.

Stage A: 1-N-benzyl-3-acetyl-1,2,5,6-tetrahydropyridine-O-2-propynyloxime.

5 g of the product obtained at stage B of example 1 is added to a solution of 1.1 g of sodium in 50 cm$^3$ of ethanol, then, at 0° C., 3.95 g of propargyl bromide is added. After heating for 3 hours to 40° C., the insoluble matter is filtered off, the solvent is evaporated, and the residue is chromatographed on silica (eluent: ethyl acetate). 4.5 g of the expected product is obtained.

Stage B: 3-acetyl-1,2,5,6-tetrahydropyridine-O-2-propynyl-oxime and its hydrochloride.

7.5 g of the product obtained at stage A is dissolved in 100 cm$^3$ of dichloroethane. After 1 hour at reflux, the solvent is evaporated, the residue is taken up with ether, the insoluble matter is filtered off and the remainder is evaporated to dryness. The residue is taken up with methanol, taken to reflux for 30 minutes, then evaporated to dryness, and the residue is taken up with a solution of sodium bicarbonate. This is extracted with ethyl acetate and the extracts are evaporated to dryness. The residue is taken up with ether and salified with gaseous hydrochloric acid. 1.25 g of the expected product is obtained. m.p. 178° C., isolated from an ether-ethanol mixture.

| Analysis: | | | |
|---|---|---|---|
| Calculated: | C% 55.94 | H% 7.04 | N% 13.05 |
| Found: | 55.72 | 7.01 | 12.99 |

EXAMPLE 7

1-methyl-3-acetyl-tetrahydropyridine-O-2-propynyloxime and its hydrochloride.

Stage A: 3-acetyl-pyridine-O-2-propynyl oxime.

5 g of 3-acetyl-pyridine is dissolved in 20 cm³ of water, 3.45 g of sodium bicarbonate and 4.45 g of ortho-2-propynyl-hydroxylamine hydrochloride in 30 cm³ of water are added, and the mixture is left for 16 hours, then heated for 3 hours at 40° C. After concentrating, it is extracted with ethyl acetate, the extracts are evaporated to dryness and purified on silica gel (eluent ethyl acetate). 5.7 g of the expected product is obtained. m.p. 156°–157° C., recrystallized from isopropanol.

Stage B: 1-N-methyl-3-acetyl-pyridine-O-2-propynyl-oxime iodide.

5.6 g of product obtained at stage A is dissolved in 60 cm³ of methanol and 8.6 g of methyl iodide is added. After 3 hours of reflux, and evaporating to dryness, the residue is taken up with a mixture of acetone and ether and filtered. 9.7 g is obtained, m.p. 150°–151° C. recrystallized from isopropanol.

Stage C: 1-methyl-3-acetyl-tetrahydropyridine-O-2-propynyl-oxime and its hydrochloride.

9.7 g of product obtained at stage B is dissolved in 100 cm³ of methanol, and 2.35 g of boron and sodium hydride is added at 0° C. After 1 hour at 0° C., then evaporating, the residue is taken up with water and extracted with ethyl acetate. The extracts are dried and evaporated to dryness. The residue is salified in ether with gaseous hydrochloric acid, and 2.7 g of the expected product is obtained. m.p. 195°–196° C., recrystallized from an isopropanol-ether mixture.

| Analysis: C₁₁H₁₆N₂O, HCl. | | | |
|---|---|---|---|
| Calculated: | C% 57.76 | H% 7.49 | N% 12.25 |
| Found: | 57.59 | 7.38 | 12.11 |

EXAMPLE 8

3-propionyl-1,2,5,6-tetrahydropyridine-oxime and its hydrochloride

Stage A: 1-N-benzyl-3-propionyl-pyridine-oxime bromide.

A mixture of 17.8 g of 3-propionyl pyridine oxime [(U.S. Pat. No. 3,004,979 (1961)] and 18 cm³ of benzyl bromide is maintained at reflux for 7 hours 30 minutes in 250 cm³ of ethyl acetate. After cooling and separating, 36.5 g of the expected product is obtained. m.p. 178°–180° C., recrystallized from an ethanol-ether mixture.

Stage B: 1-N-benzyl-3-propionyl-1,2,5,6-tetrahydropyridineoxime.

36.2 g of product obtained at stage A is dissolved in 250 cm³ of methanol, and the temperature is maintained at 10° C. while 6.4 g of boron and sodium hydride is added in portions, with agitation for 3 hours. After evaporating under reduced pressure, the residue is taken up with water, and extracted with ethyl acetate. The extracts are dried and the solvent is evaporated. The residue is purified by chromatography on a column (eluent: ethyl acetate) and 21 g of the expected product is obtained. m.p. 111°–112° C., recrystallized from ethyl acetate.

Stage C: 1-N-benzyl-3-propionyl-1,2,5,6-tetrahydropyridine-O-trimethyl-silyl-oxime.

6 g of the product obtained at stage B, 70 cm³ of benzene and 2.95 g of 1,4-diazabicyclo[2.2.2.] octane are mixed together. 3.23 cm³ of trimethylsilyl chloride is added, and the whole is taken to reflux for 3 hours, then cooled. The insoluble matter is filtered off, the solvent is evaporated, and the residue is taken up with ether. The insoluble matter is filtered off and the remainder is evaporated to dryness. 7.5 g of the expected product is obtained. b.p.: 250° C. under 0.06 mbar).

Stage D: 3-propionyl-1,2,5,6-tetrahydropyridine oxime and its hydrochloride.

16 g of the product obtained at stage C is dissolved in 150 cm³ of dichloroethane, and after cooling to 0° C., 16.2 g of alpha-chloro-ethyl chloroformate is added and the whole is maintained at reflux for 3 hours, then the solvent is evaporated off. The residue is taken up with ether, filtered, and concentrated to dryness. The residue is taken up with 100 cm³ of methanol, and taken to reflux for 6 hours. The methanol is evaporated off, and the remainder is pruified by passage through alumina (eluent: chloroform-methanol 7-3, then methanol alone). After evaporating to dryness, the residue is taken up with ethanol, filtered on charcoal and precipitated by adding hexane. The precipitate is filtered and, after purification in an ethanolhexane mixture, 1.3 g of the expected product is obtained. m.p. 205°–206° C. Using the process of example 2, the expected hydrochloride is obtained.

| Analysis: C₈H₁₄N₂O. HCl. | | | |
|---|---|---|---|
| Calculated: | C% 50.39 | H% 7.93 | N% 14.69 |
| Found: | 50.08 | 7.87 | 14.48 |

EXAMPLE 9

3-propionyl-1,2,5,6-tetrahydropyridine-O-methyl-oxime and its hydrochloride.

Stage A: 1-N-benzyl-3-propionyl-1,2,5,6-tetrahydropyridine-O-methyl-oxime.

6.11 g of the product obtained at stage B of example 8 is added to a solution of 1.2 g of sodium in 80 cm³ of ethanol. 1.58 cm³ of methyl iodide is added, the whole is taken to reflux for 6 hours, then cooled and concentrated to dryness under reduced pressure. The residue is taken up with water and extracted with ethyl acetate. The extracts are dried, evaporated to dryness, and the residue is chromatographed (eluent: ethyl acetate-toluene 6-4), so obtaining 2.5 g of the expected product. (m.p. 170° C. at 0.05 mbar).

Stage B: 3-propionyl-1,2,5,6-tetrahydropyridine-O-methyl-oxime and its hydrochloride.

3.5 g of product from stage A is dissolved in 50 cm³ of chloroethane, and at 0° C., 2.04 g of alpha-chloro-ethyl chloroformate is added. After 3 hours at reflux, the solvent is evaporated off, the residue is taken up with ether, filtered and evaporated to dryness. The residue is taken up with 30 cm³ of methanol and taken to reflux for 30 minutes, then evaporated to dryness. The residue is recrystallized from a mixture of ethanol and ether, and 1.17 g of the expected product is obtained. m.p. 210°-212° C.

Using the process of example 2, the expected hydrochloride is obtained.

| Analysis: $C_9H_{16}N_2O$, HCl. | | | |
|---|---|---|---|
| Calculated: | C% 52.53 | H% 8.26 | N% 13.56 |
| Found: | 52.80 | 8.37 | 13.68 |

EXAMPLE 10

1-N-carboxyethyl-3-acetyl-1,2,5,6-tetrahydropyridine-O-methyl-oxime 1.8 g of the product obtained at example 3 is dissolved to 30 cm³ of benzene at 5° C., then 1.63 cm³ of triethylamine and 1.12 cm³ of ethyl chloroformate are added. After agitating for 30 minutes at ambient temperature, washing with water, evaporating to dryness and rectifying, 2.56 g of the expected product is obtained. (b.p. 155° C. under 0.07 mbar).

| Analysis | | | |
|---|---|---|---|
| Calculated: | C% 58.39 | H% 8.02 | N% 12.38 |
| Found: | 58.41 | 7.88 | 12.29 |

EXAMPLE 11

1-N-carboxy-benzyl-3-acetyl-1,2,5,6-tetrahydropyridine-O-methyl-oxime 2.5 g of product obtained at stage B of example 3 is dissolved in 40 cm³ of anhydrous benzene, 2.7 cm³ of benzyl chloroformate is added; the mixture is taken to reflux for 1 hour, then cooled, washed with 10 cm³ of 5% hydrochloric acid and dried, and the solvent is evaporated. The benzyl chloride formed is eliminated, and 2.3 g of the expected product is obtained, recrystallized from cyclohexane. m.p. 90° C.

| Analysis | | | |
|---|---|---|---|
| Calculated: | C% 65.68 | H% 6.61 | N% 10.21 |
| Found: | 65.81 | 6.58 | 10.17 |

EXAMPLE 12

1-N-hydroxyl-3-acetyl-1,2,5,6-tetrahydropyridine-O-methyl-oxime 3.5 g of 3-acetyl-pyridine-O-methyl-oxime-N-oxide [J. Heterocyclic Chem. 16 1459, (1979)] is dissolved in 50 cm³ of methanol and cooled to −10° C. 2.4 g of boron and sodium hydride is added, with agitation for 2 hours at ambient temperature followed by evaporation to dryness. The residue is taken up with water and extracted with ethyl acetate. The extracts are dried, evaporated to dryness, and purified by chromatography on silica gel, (eluene: ethyl acetate). 2.85 g of the expected product is obtained. m.p. 94°-96° C., after crystallizing from hexane.

| Analysis | | | |
|---|---|---|---|
| Calculated: | C% 56.45 | H% 8.29 | N% 16.46 |
| Found: | 56.28 | 8.32 | 16.31 |

EXAMPLE 13

1-methyl-3-cyclopropylcarbonyl-1,2,5,6-tetrahydropyridine-O-methyl-oxime and its benzene sulphonate Stage A: 3-pyridyl-cyclopropylcetone-O-methyl-oxime.

2.03 g of methoxylamine hydrochloride is added to a solution of 3.5 g of 3-pyridyl-cyclopropylcetone in 50 cm³ of methanol. After heating to reflux for 4 hours, the solvent is evaporated off and the remainder is taken up with an aqueous solution of sodium bilcarbonate. This is extracted with methylene chloride, the extracts are dried then evaporated, and 4.1 g of the expected product is obtained.

Stage B: 1-methyl-3-cyclopropylcarbonyl-pyridine-O-methyl oxime iodide.

4 g of the product obtained at stage A is added to a solution of 5.3 g of methyl iodide in 50 cm³ of methanol, and taken to reflux for 3 hours. After evaporating to dryness, the residue is triturated in a mixture of ethanol and ether, then filtered, and 6.6 g of the expected product is obtained, recrystallized from isopropanol. m.p. 133° C., (decomposes).

| Analysis: $C_{11}H_{15}IN_2O$ | | | |
|---|---|---|---|
| Calculated: | C% 41.52 | H% 4.75 | N% 8.80 |
| Found: | 41.17 | 4.66 | 8.76 |

Stage C: 1-methyl-3-cyclopropylcarbonyl-1,2,5,6-tetrahydropyridine-O-methyl-oxime and its benzene sulphonate.

To a solution of 6.4 g of product obtained at stage B in 70 cm³ of methanol, 1.52 g of boron and sodium hydride is introduced at 0° C., and the mixture is allowed to rect for 1 hour 30 minutes at ambient temperature, then evaporated. The residue is taken up with water, and extracted with ethyl acetate. The extracts are dried, evaporated to dryness, and purified by elution on alumina (eluent: toluene-ethyl acetate 6-4). After distilling at 160° C. under 0.2 mm of mercury, 2.45 g of the base obtained is taken up in 100 cm³ of benzene with 1.994 g of benzene sulphonic acid, evaporated to dryness, triturated in a little ethyl acetate, filtered, and 1.7 g of the expected product is obtained. m.p. 76° C. (decomposes).

| Analysis: $C_{11}H_{18}N_2O$, $C_6H_5SO_3H$ | | | |
|---|---|---|---|
| Calculated: | C% 57.93 | H% 6.86 | N% 7.95 |
| Found: | 58.04 | 6.94 | 7.87 |

| Examples of Pharmaceutical Compositions | |
|---|---|
| a) Tablets were prepared of the following formula: | |
| Product of example 3 | 200 mg |
| Excipient q.s. for a tablet finished at | 300 mg |
| (Detail of excipient: lactose, corn starch, treated starch rice starch, magnesium stearate, talc). | |
| b) Capsules were prepared of the following formula: | |
| Product of example 1 | 100 mg |
| Excipient q.s. for a capsule terminated at | 300 mg |
| (Detail of excipient: talc, magnesium stearate, aerosil). | |
| c) Tablets were prepared of the following formula: | |
| Product of example 2 | 50 mg |
| Excipient q.s. for a tablet finished at | 300 mg |
| (Detail of excipient: lactose, corn starch, treated starch, | |

-continued

Examples of Pharmaceutical Compositions rice starch, magnesium stearate, talc).

d) Tablets were prepared of the following formula:

| | |
|---|---|
| Product of example 12 | 50 mg |
| Excipient q.s. for a capsule terminated at | 300 mg |

(Detail of excipient: lactose, corn starch, treated starch, rice starch, magnesium stearate, talc).

Biological activity

The products have been utilized in the hydrochloride form.

Acute toxicity

The test was carried out on male mice (CD$_1$ Charles Rivers) of 22 to 24 g, fasting for 16 hours. The products are administered by oral route at doses of 1000, 500, 250, 125, 62 and 31 mg/kg. The mortality is noted during the 7 days following the treatment.

| Product of Example | LD$_{50}$ in mg/kg |
|---|---|
| 1 | 350 |
| 2 | 350 |
| 3 | 125 |
| 12 | 175 |
| Arecoline HBr | 600 |

Test on ileum isolated from guinea-pig

Pieces of the ileum are removed from guinea-pigs killed by decapitation. The isolated ileum is placed in 10 cm$^3$ of Tyrode's solution at 37° C. and aerated with a mixture of oxygen (95%) and carbon dioxide gas (5%). The contractions due to the products are recorded by means of a detector connected to a polygraph. The products to be tested are added at concentrations between $1.10^{-3}$ M/l and $1.10^{-8}$ M/l.

The products presenting a contraction effect are tested relative to atropine and hexamethonium to establish whether the activity is of the "muscarine" or "nicotine" type.

The agonist activity is expressed in pD$_2$ (negative logarithm of the dose which produces 50% of the maximum effect.

| Example | pD$_2$ |
|---|---|
| 1 | 5.25 |
| 2 | 4.85 |
| 3 | 7.50 |
| 12 | 5.39 |
| Arecoline | 6.48 |

Dioarrhoeic activity

The test is carried out on male mice (CD$_1$, Charles Rivers) weighing 25 to 30 g, fasting for 6 hours. The product dissolved at 5% in methocel is administered by oral route, by means of an oesophagic probe.

The control animals receive only the excipient.

After treatment, the animals are put separately in cages the base of which is covered with blotting paper and are put under observation for 30, 60, 120 and 180 minutes.

The sheets of absorbent paper are changed after each observation.

The consistency of the feces is evaluated according to the method of Randall and Baruth (Arch. Int. Pharmacodyn. 220, 94, 1976) and accoding to the following scale of values:

0: firm consistency
1: feces slightly soft with or without humid aureola.
2: feces slightly soft with presence of a well defined humid circle.
3: feces soft with presence of a large humid circle.
4: feces without consistency with presence of a very large humid circle.

For each product, the dose was noted which caused a diarrhoea in 50% of the animals according to the method of Miller and Tainter (Proc. Soc. Exp. Biol. Med. 57, 261, 1944).

| Example | ED$_{50}$ in mg/kg |
|---|---|
| 1 | 5 |
| 2 | >100 |
| 3 | 0.85 |
| 12 | 1 |
| Arecoline | 35 |

Hypothermic activity

The test is carried out on male mice (CD$_1$ Charles Rivers), weighing 25-30 g, fasting for 6 hours.

The temperature of the body is noted by means of a thermocouple placed in the rectum to about 1.5 cm and connected to an electric temperature recorder.

The products are administered by oral route or subcutaneously and the temperatures are noted at the instant 0 and 30 minutes, 1 hour, 2 hours and 2-and-a-half hours after treatment.

The degree of hypothermia is evaluated as the difference between the treated animals and the controls, and the dose necessary to reduce the body temperature by 1° C. is determined.

| Example | Effective dose (−1° C.) in mg/kg | |
|---|---|---|
| | per os | s.c. |
| 1 | 9 | 11 |
| 2 | 12 | 25 |
| 3 | 0.87 | 0.91 |
| 12 | 0.77 | 0.72 |
| Arecoline | 194 | 3 |

The duration of action of the products has been evaluated by using the dose which reduces the body temperature by 1° to 1.5° C.

| Product of Example | Dose mg/kg | Admin. route | Variation of the Body Temperature Times in minutes after treatment | | | | |
|---|---|---|---|---|---|---|---|
| | | | 0 | 30 | 60 | 120 | 180 |
| 1 | 10 | p.o. | 0 | −0.7 | −1.0 | −0.2 | +0.1 |
| | 10 | s.c. | 0 | −0.6 | −0.8 | −0.2 | 0 |
| 2 | 20 | p.o. | +0.1 | −1.3 | −1.3 | −0.9 | 0 |
| | 40 | s.c. | +0.1 | −1.0 | −1.4 | −1.1 | −0.8 |
| 3 | 1 | p.o. | +0.1 | −1.1 | −1.0 | −0.1 | −0.1 |
| | 1 | s.c. | +0.1 | −1.0 | −0.8 | +0.1 | +0.1 |
| 12 | 1 | p.o. | 0 | −1.3 | −1.1 | 0 0 | 0 |
| | 1 | s.c. | −0.1 | −1.4 | −1.3 | +0.1 | 0 |
| Arecoline Hbr | 200 | p.o. | +0.1 | −1.1 | −1.0 | −0.2 | −0.1 |
| | 3.5 | s.c. | −0.1 | −1.5 | −0.1 | +0.2 | +0.2 |

We claim:

1. Compounds of the formula (I):

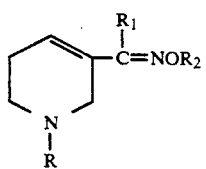

in which R represents hydrogen, $R_1$ represents a linear, branched or cyclic alkyl, alkenyl or alkynyl containing up to 8 carbon atoms and $R_2$ represents alkyl containing up to 8 carbon atoms, as well as their pharmaceutically acceptable addition salts with acids.

2. Compounds of the formula (I) as defined in Claim 1, in which $R_1$ represents a linear alkyl containing from 1 to 4 carbon atoms, as well as their addition salts with acids.

3. Compounds of the formula (I) as defined in claim 2, in which $R_1$ represents methyl, as well as their addition salts with acids.

4. Compounds of the formula (I) as defined in any one of the claims 1 to 3, in which $R_2$ represents an alkyl radical containing from 1 to 4 carbon atoms.

5. 3-acetyl-1,2,5,6-tetrahydropyridine-O-methyl-oxime and its hydrochloride.

6. A therapeutic composition for the treatment of Alzheimer's disease, senile dementia or memory disorders in the aged, susceptible to treatment with cholinergics or muscarinic agents, comprising a cholinomimetically effective amount of a compound as defined in any one of claims 1-3 or 5 and a therapeutically acceptable carrier.

7. A method for the treatment of a patient suffering from Alzheimer's disease, senile dementia or memory disorder in the aged, susceptible to treatment with cholinergic or muscarinic agents, comprising administering to the patient a cholinomimetically effective amount of a compound as defined in any one of claims 1-3 or 5.

* * * * *